United States Patent [19]
Owens

[11] Patent Number: 5,882,731
[45] Date of Patent: Mar. 16, 1999

[54] METHOD OF APPLYING A MILDEWCIDE LADEN FILM AND COMPOSITION FOR THE USE THEREWITH

[76] Inventor: Richard L. Owens, 1318B Olympic Ct., Conyers, Ga. 30012

[21] Appl. No.: 899,397

[22] Filed: Jul. 23, 1997

[51] Int. Cl.$^6$ .............................. B05D 3/00; A01N 25/02; A01N 29/00; A01N 31/02
[52] U.S. Cl. .................. 427/353; 106/18.21; 106/18.32; 106/18.33; 106/18.34; 106/18.35; 424/78.09; 424/405; 424/407; 514/372; 514/394; 514/478; 514/646; 514/649; 514/709
[58] Field of Search .............................. 106/18.29, 18.32, 106/18.33, 18.34, 18.35; 427/353; 514/372, 394, 478, 646, 649, 709; 424/78.09, 405, 407

[56] References Cited

U.S. PATENT DOCUMENTS

| | | | |
|---|---|---|---|
| 1,881,128 | 10/1932 | Payne et al. | 106/18.29 |
| 2,021,137 | 11/1935 | Stone | 99/3 |
| 2,292,323 | 8/1942 | Ingle | 99/178 |
| 2,349,434 | 5/1944 | Hyman | 514/765 |
| 2,416,460 | 2/1947 | Smith et al. | 514/164 |
| 2,476,235 | 7/1949 | Benignus | 514/311 |
| 2,486,961 | 11/1949 | Meyer | 117/138.5 |
| 2,818,344 | 12/1957 | Buckman | 106/15 |
| 2,970,081 | 1/1961 | McCall et al. | 167/30 |
| 3,116,969 | 1/1964 | Coleman | 21/74 |
| 3,912,674 | 10/1975 | Stahl | 524/272 |
| 3,918,981 | 11/1975 | Long | 106/15.05 |
| 4,159,883 | 7/1979 | Mizell | 401/201 |
| 4,183,757 | 1/1980 | Groszek et al. | 106/14.11 |
| 4,347,266 | 8/1982 | Norman et al. | 427/154 |
| 4,398,953 | 8/1983 | Van Der Linde | 106/10 |
| 4,410,363 | 10/1983 | Supcoe et al. | 106/18.29 |
| 4,433,020 | 2/1984 | Narukawa et al. | 428/113 |
| 4,525,501 | 6/1985 | Norman et al. | 524/28 |
| 4,612,058 | 9/1986 | Geke et al. | 134/38 |
| 4,612,255 | 9/1986 | Hein | 428/541 |
| 4,749,411 | 6/1988 | Chapin | 106/10 |
| 4,750,919 | 6/1988 | Patzelt et al. | 55/45 |
| 4,806,263 | 2/1989 | Leathers et al. | 252/106 |
| 4,950,329 | 8/1990 | McIntyre et al. | 106/15.05 |
| 5,028,458 | 7/1991 | Mineck | 427/355 |
| 5,045,366 | 9/1991 | Sedun | 427/440 |
| 5,264,250 | 11/1993 | Steele et al. | 427/380 |
| 5,338,345 | 8/1994 | Scarborough et al. | 106/2 |
| 5,366,767 | 11/1994 | Howard | 427/294 |
| 5,385,604 | 1/1995 | Ainslie | 106/15.05 |
| 5,385,750 | 1/1995 | Aleksejczk et al. | 427/4 |
| 5,460,644 | 10/1995 | Thomassen | 106/18.32 |

FOREIGN PATENT DOCUMENTS

| 57-141467 | 9/1992 | Japan . |
|---|---|---|
| 57-141468 | 9/1992 | Japan . |

*Primary Examiner*—Anthony Green
*Attorney, Agent, or Firm*—Price, Heneveld, Cooper, DeWitt & Litton

[57] ABSTRACT

A method is disclosed for applying a mildewcide compound laden film to surfaces by applying an aqueous, film-depositing composition onto said surfaces, allowing to stand momentarily, and rinsing with water. After rinsing, a residual, durable, virtually invisible film remains. This film is mildew resistant, paintable and its sheen closely mimics that of the surfaces prior to application of the aqueous composition. The aqueous composition comprises a mildewcide compound, a non-ionic surfactant, water, and at least one film-former.

31 Claims, No Drawings

METHOD OF APPLYING A MILDEWCIDE LADEN FILM AND COMPOSITION FOR THE USE THEREWITH

CROSS-REFERENCE TO RELATED APPLICATIONS

The Applicant herein claims the benefit of priority under 35 U.S.C. § 119(e) to U.S. Provisional Application No. 60/022,570 entitled, "METHOD OF APPLYING A MILDEWCIDE LADEN FILM AND COMPOSITION FOR USE THEREWITH," which was filed on Jul. 24, 1996 by Richard L. Owens, the entire disclosure of which is hereby incorporated by reference.

FIELD OF INVENTION

This invention relates to a method for applying a substantially invisible mildew resistant coating and composition for use therewith.

BACKGROUND OF THE INVENTION

Mildew is a problem the world over. Any warm, damp surface is an open invitation for airborne mildew spores to take root and grow. Growing rapidly in the right environment, mildew quickly become visible as dark black-green spots.

Whether in a bath, closet, basement or on outside walls, mildew is an unwelcome guest. Homeowners in particular fight to remove this stubborn unsightly fungus.

Thankfully, there are products available in the retail market for killing mildew and bleaching stains caused by mildew. Most widely used are chlorine-containing compositions. Regular cleaning with these compositions can control the mildew, but multiple cleanings can damage painted surfaces by removing some of the paint and roughening the surface. Eventually, those areas dry and crack allowing water to more easily penetrate past the protective paint. The resulting moisture-laden cracks are the prefect environment for mildew regrowth.

It is desirable to both inhibit this regrowth and limit the possible damage caused by repeated harsh cleanings.

A solution to both problems has evolved over the last twenty years whereby concentrated mildewcide "additives" are purchased by the consumer and mixed with coatings prior to application.

However, this method of mildew control is not without problems. Among them are:

1. An E.P.A. requirement that all mildewcide additives be registered in every state in which they are sold.
2. The likelihood of confusion as to concentration. The recommended dosage for one product is only nine grams while that of another is almost ninety grams.
3. Freedom for consumers to add too much or too little product which can lead to too little protection, yellowing, chalking, or graying of the dried coating.
4. Finite length of time an additive will be effective. The U.S. Navy tests of 1985–1986 and the National Bureau of Standards tests of 1975–1976 show that tested additives began losing effectiveness within months after outdoor exposure in hot, humid climates.
5. The cost of labor and materials required to recoat for the sole purpose of controlling mildew can often be exorbitant.

Among the mildewcidal and fungicidal products and treatment methods which have been developed are various inventions. These include:

1. U.S. Pat. No. 2,476,235 to Benignus discloses a soaked-in or brushed-on treatment for fibrous materials and textiles to imbue long-term fungal resistance under weathering conditions. The fungicide is a metallic salt of hydroxyquinoline or pentachlorophenate in a modified alkyd resin which may contain an aqueous wax suspension to provide waterproofing to the treated surface.
2. U.S. Pat. No. 2,486,961 to Meyer describes an aqueous or nonaqueous bath for imparting mildew-resistance to cellulose textiles. Dihydroxybenzophenone-based mildewcides are used as the active ingredient. The composition may contain a water-repellant such as a wax emulsion.
3. U.S. Pat. No. 2,818,344 to Buckman discloses mildew-resistant paint compositions using barium borates and/or barium borosilicates in an oil or oil emulsion vehicle.
4. U.S. Pat. No. 2,970,081 to McCall et al. discloses a fungistatic and bacteriostatic soap, wax polish, or plastic composition in which the active ingredient is an aromatic hydroperoxide.
5. U.S. Pat. No. 3,116,969 to Coleman teaches a fungicidal, tacky aqueous coating as a dip or spray to treat air filters. This employs quaternary ammonium salts as an antimicrobial.
6. U.S. Pat. No. 3,918,981 to Long describes a fungicidal coating, a method of surface application, and mildew-resistant paper products produced thereby. This composition employs metal salts of quinolinolate, and a binder of a wax or wax-resin emulsion especially one containing paraffin wax.
7. U.S. Pat. No. 4,183,757 to Groszek et al. teaches an aqueous wax emulsion which is brushed or sprayed on as a biocidal coating to be used on underwater surfaces to combat bacterial and algal growth.
8. U.S. Pat. Nos. 4,347,266 and 4,525,501 to Norman et al. discloses an aqueous, anti-soiling pre-coat spray of polymer for use on water-resistant articles. It is used to form a sacrificial undercoat film on, e.g., automobiles. This composition may contain a little biocide such as orthophenoxyphenol.
9. U.S. Pat. No. 4,612,255 to Hein describes a waterproofing and preserving composition for use on permeable substrates such as wood, fiber, and concrete. An aqueous dispersion of saturated hydrocarbon wax is mixed with an oil-soluble metal salt of a carboxylic acid. The latter has fungicidal properties. A moldicide may also be added. Hein also disclosed a method of treatment, and his composition may be brushed, sprayed, painted, or used as a dip or soak or for pressurized or vacuum-treatment.
10. U.S. Pat. No. 4,749,411 to Chapin discloses a high-gloss, germicidal, hard surface buffing composition comprising a solution of a solid waxy polyethylene glycol and a somewhat fungicidal quaternary ammonium chloride compound.
11. U.S. Pat. No. 5,028,458 to Mineck teaches a non-wax, antiseptic polish in which the active ingredient is the microbicide, Povidone-Iodine.
12. U.S. Pat. No. 5,045,366 to Sedun discloses a method for protecting wood from fungi and mold using an environmentally safe antifungal composition. The fungicide is one of the alkyl sulfosuccinates which is combined with an adjuvant and an oil, such as paraffinic mineral oil, and may also contain an antifoaming agent. An aqueous liquid wash concentrate or a powdered concentrate is produced. When diluted, this product is sprayed or used as a dip for freshly cut wood.

13. U.S. Pat. No. 5,264,250 to Steele et al. discloses an antimicrobial hydrophilic coating for heat exchanger surfaces and a method of application. An inorganic wetting agent such a silica or a silicate is combined with an inorganic binder and an antimicrobial agent such as silver oxide. The resulting slurry is sprayed or painted or dipped onto heat exchangers such as are used in zero-gravity environments.

14. U.S. Pat. No. 5,338,345 to Scarborough et al. teaches an aqueous water repellant coating, its method of manufacture, and its method of use. It is comprised of an organic water-repellant composition containing oil, wax, or an organometallic wax and a modified polyacrylate polymer emulsifier. An antimildew preservative may be added to the composition.

15. U.S. Pat. No. 5,366,767 to Howard teaches the use of sodium silicate and a surfactant in aqueous solution to kill and prevent moss and fungi growth on porous surfaces such as roofing material, ceramic, wood siding, concrete, and asphalt. He also discloses a method of spray application and notes that prior art describes the use of zinc and copper ion-based algicidal and fungicidal coatings on roofing granules (citing U.S. Pat. No. 3,888,684 to Little).

16. U.S. Pat. No. 5,460,644 to Thomassen discloses aqueous mildew-resistant coating compositions. These are used as clear or pigmented paints or as stain-blocking primers. The composition contains an organic mildewcide which is, e.g., isothiazolinone-based.

Though applied in many ways, none of the above referenced patents teaches an alternative to the apply and dry method. Furthermore, the important issue of surface "sheen" and dried coating "sheen" is not broached therein. A specific example of sheen mismatch involves applying a clear coating which dries "flat" (i.e. to low or no luster) on both a high gloss (shiny luster) surface and a flat surface in the same operation. The flat dried coating upon the flat surface is virtually invisible. However, the flat dried coating upon the high gloss surface would be easily visible especially if viewed from the side. None of the above references addresses this problem.

SUMMARY OF THE INVENTION

It is an object of this invention to provide a new method for applying a durable mildewcide compound-laden film to surfaces.

It is a further object of this invention to provide a composition to use with said method such that, when applied to surfaces, allowed to stand momentarily (20–90 seconds), and rinsed, will leave a durable, clear, mildew-resistant film.

It is a further object of this invention to provide a mildew resistant composition such that the sheen of the above described dry film mimics the sheen of the surface upon which it has been applied. It is still another object of this invention that the above described film be paintable.

Surprising, it has been found that a composition meeting these object is a film-depositing aqueous solution comprising: 1) at least one film-former, 2) at least one mildewcide compound, and 3) at least one non-ionic surfactant.

DEFINITION OF TERMS

For purposes of this application the following terms are defined:

1. Apply: To put on or spread on via brush, roller, spray apparatus or by dipping.
2. Mildewcide Compound: Any substance that kills or inhibits the growth of mildew or its spores.
3. Mildewcide Compound-Containing Mixture: Any mixture, especially a commercially available mixture, containing at least one mildewcide compound.
4. Laden: Having added to; loaded, enriched.
5. Film: A fine, thin skin, surface, layer, or coating.
6. Surfaces: The outer faces or exteriors of either flexible or rigid objects.
7. Durable: Lasting or continuing to exist after having been repeatedly subjected to low-pressure water spray.
8. Mildew Resistant: Retarding, hindering or opposing the growth of mildew.
9. Paintable: The ability to be uniformly and durably coated with a mixture of a pigment with oil, water etc. in a liquid form applied using a brush, roller, or spray gun.
10. Sheen: Shininess or luster.
11. Mimic: Inclined to copy, imitate, or closely resemble.
12. Sacrificial: Having the nature to allow destruction or permit injury to.
13. Film-Former: A substance which may be dissolved or suspended in an aqueous solution, and upon application of said solution or suspension to a solid surface, will be deposited as a film which remains upon said surface when rinsed about 20 to about 90 seconds after application. Examples include waxes, wax-fat mixtures, and wax-fat-silicone mixtures which are dissolvable or suspendable in an aqueous solution.
14. Film-Depositing Composition: A film-former-containing composition that is able to deposit said film-former(s) as a film upon a surface where that composition is applied to the surface and that surface is then rinsed within about 20 to about 90 seconds after application of the composition, and where that film remains after this rinsing.
15. Wax: A plastic substance which is typically harder when cold and easily molded when warm. Any waxlike substance yielded by plants or animals. Any of a group of substances with a waxy appearance made up variously of esters, fatty acids, free alcohols, and solid hydrocarbons.
16. Natural Wax: Any waxlike substance yielded by or derived from plants or animals.
17. Paraffinic Wax: A waxy solid substance consisting of a mixture of straight-chain, saturated hydrocarbons obtained chiefly from the distillation of petroleum.
18. Invisible: That cannot be seen; not apparent; imperceptible; indistinct by simply viewing with the human eye.

DETAILED DESCRIPTION OF THE PREFERRED EMBODIMENTS

MILDEWCIDE SELECTION

A necessary requirement of this invention is that the residual film be mildew resistant. Consequently, great care was taken to choose the most appropriate mildewcide compound(s) from those available. A helpful source of information concerning mildewcide performance came from official U.S. Navy tests. The Port Hueneme, California, U.S. Naval Air Engineering Laboratory conducted field performance tests on EPA-approved mildewcide compound-containing mixtures in Panama, Central America in 1985–1986. Only those tested in "latex" (water based) formulations were considered for purposes of this Application.

| MIXTURE TRADE NAME | NAVY RATING | MIXTURE TRADE NAME | NAVY RATING |
|---|---|---|---|
| 1. Troy Polyphase | Superior | 9. Skane M8 | Fair |
| 2. Nopscocide N-96 | Superior | 10. Amical 81 | Fair |
| 3. Busan 1030 | Good | 11. Metasol TK100 | Fair |
| 4. Intercide PMA18 | Good | 12. Intercide 34 DA | Fair |
| 5. Intercide 60 | Good | 13. Diall (TBTO) | Fair |
| 6. Nuodex Super Ad-It | Good | 14. Cotin 234 (Tin) | Fair |
| 7. Intercide MDS | Good | 15. Tektamar 38AD | Poor |
| 8. Amical 48 | Good | 16. Busan 11-M1 | Poor |
| | | 17. Vancide 51Z | Poor |

Of the latex formulations presented in the Naval test data, numbers 4, 5, 6, 7, 12, 13, 14, and 17 contained heavy metal and were deemed unacceptable for purposes of the invention disclosed herein because of extensive restrictions placed on them by the E.P.A. and other governing agencies. Nopscocide N-96, Amical 48, and Amical 81 were effective mildewcides, but were eliminated from further testing because under intense sunlight they tend to cause certain coatings to "yellow" or "gray." Therefore, only the remaining mixtures were considered for further evaluation.

Of these remaining products, even though Metasol TK100 has proven effective as a paint additive, it precipitated out of solution too easily to be highly preferred for purposes of this invention. Of the other products, only Busan 1030 and Troy Polyphase were found to be most preferred, because of disparity in performance of the other products compared to these two, as described below. However, Metasol TK100 (and its active ingredient, 2-(4-Thiazolyl) benzimidazole), as well as a number of other mildewcide compounds are useful in the present invention, either as replacements for or supplements to the active ingredients found in the Busan 1030 and Troy Polyphase products. These include 2,4,5,6,-Tetrachloro-isophthalonitrile, 2-N-Octyl-4-isothiazolin-3-one, and Diiodomethyl p-tolyl sulfone, as well as products containing these mildewcide compounds.

Therefore, by the process of elimination, only two mildewcide compound-containing mixtures, those containing what appeared to be the most preferred mildewcide compounds, were chosen for further evaluation:

Troy Polyphase (active ingredient: 3-Iodo-2-propynyl-butyl carbamate) and Two different outside labs were supplied with a number of code-labeled samples of a clear, acrylic sealer. Each sample, containing various percentages of either Busan 1030 or Troy Polyphase P20T, was tested for mildew resistance. Both exterior and chamber testing were conducted. Busan 1030 proved to outperform the Troy Polyphase P20T even when used at a lower dosage in these tests.

COMPOSITION SELECTION

In order to develop mildewcidal compositions which were film-depositing, numerous formulas for wash and wax concentrations were obtained from General Electric, Dow Corning, and others. Also, available retail products were purchased. After dilution with water as specified by the manufacturer, samples of these were used to test:

1. Film durability after spray application to various substrates;
2. Ability to mimic the sheen of difference substrates after application;
3. Recoatability of treated surfaces using latex and alkyd based paints; and
4. Dissolvability of Busan 1030 in the aqueous dilution.

Those formulas based on paraffinic waxes were found to be neither as durable nor as paintable as those based on natural waxes. As a result, only natural-wax based and natural-wax-derivative-based formulations were further developed. Among these formulations, those containing, in addition to at least one such wax, at least one fatty amine and at least one amino silicone were found to leave clear, highly durable films. Consequently, a preferred embodiment of the present invention comprises:

1. At least one wax. The preferred waxes are natural waxes, more preferably carnauba wax. The concentration of wax in the composition is preferably about 0.1% to about 2% wt/wt, more preferably about 0.2% to about 0.5% wt/wt.
2. At least one fatty amine, preferably at least one fatty amine conforming to the following structure:

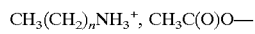

wherein n is an integer ranging from 15–19, preferably 17. The concentration of fatty amine in the composition is preferably about 0.01% to about 2% wt/wt, more preferably about 0.05% to about 0.1% wt/wt.

3. At least one amino silicone, preferaby at least one amino silicone conforming to the following structure:

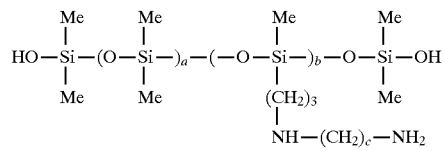

wherein: Me is a methyl group ($-CH_3$); a is 100–1000, preferably 150–500; b is 1–10, preferably 2–5; and c is 2–4, preferably 2. The concentration of amino silicone in the composition is preferably about 0.01% to about 1%, more preferably about 0.1% to about 1%.

4. At least one mildewcide compound selected from:
   a. 2-(Thiocyanomethylthio) benzothiazole, the active ingredient in, e.g., the Busan 1200 or 1030 mildewcide compound-containing mixtures;
   b. 3-Iodo-2-propynyl butyl carbamate, the active ingredient in, e.g., the Troy Polyphase P20T mildewcide compound-containing mixture;
   c. 2,4,5,6,-Tetrachloro-isophthalonitrile, the active ingredient in, e.g., the Tuffcide 500 mildewcide compound-containing mixture;
   d. 2-(4-Thiazolyl) benzimidazole, the active ingredient in, e.g., the Metasol TK100 mildewcide compound-containing mixture;
   e. 2-N-Octyl-4-isothiazolin-3-one, the active ingredient in, e.g., the Skane M-8 mildewcide compound-containing mixture;
   f. Diiodomethyl p-tolyl sulfone, the active ingredient in, e.g., the Amical Flowable mildewcide compound-containing mixture; and
   g. Mixtures thereof.

The preferred mildewcide compound is 2-(Thiocyanomethylthio) benzothiazole.

Preferably, the concentration of mildewcide compound is at least about 0.05% wt/wt. When the mildewcide compound is provided by a (e.g., commercially available) mildewcide compound-containing mixture, the concentration of such mixture will preferably be at least about 0.5%, and more preferably about 0.5% to about 10% wt/wt, of the composition. Where the source of said mildewcide compound is a mildewcide compound-containing mixture containing either 2-(Thiocyanomethylthio)benzothiazole or 3-Iodo-2-propynyl butyl carbamate or a mixture thereof, preferably about 4% to about 7% wt/wt of said mixture is used in the composition; preferably, the composition contains about 0.4% to about 2.5% wt/wt of either 2-(Thiocyanomethylthio)benzothiazole or 3-Iodo-2-propynyl butyl carbamate or a mixture thereof.

5. At least one non-ionic surfactant, preferably at least one non-ionic surfactant conforming to the following structure:

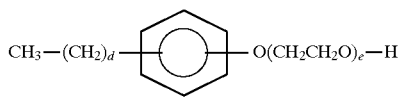

wherein: d is an integer ranging from 5 to 12, preferably 9; and e is an integer ranging from 4 to 12, preferably 9. The concentration of surfactant is preferably about 0.1% to about 5% wt/wt, more preferably about 0.5% to about 1% wt/wt. And 6. An aqueous solvent, preferably water or an aqueous solution, and most preferably water (the balance). Typically about 85% to about 99% water may be used.

EXAMPLE 1
COMPOSITION FORMULATION

A formula from Dow Corning was slightly modified and diluted to 4% in a 2% (final concentation) aqueous Busan 1030 solution to create a preferred embodiment:

A. Concentrate Ingredients:

| | | |
|---|---|---|
| 1. | Carnauba Wax (T3 Flakes) | 6.60% |
| 2. | Armac HT Flakes (Hydrogenated tallowamine acetates) | 2.00% |
| 3. | Water | 58.00% |
| 4. | Dow Corning 929 | 33.40% |
| | (Cationic Emulsion) | 100.00% |

B. Preparation of Concentrate:
1. Melt Carnauba wax with Armac at 205° F.
2. Heat water to 194° F. (90° C.) and mix with wax and armac HT while stirring continuously.
3. Cool to room temperature.
4. Add Dow Corning 929.
Final Dilution:

| | | |
|---|---|---|
| 1. | Water | 92.5% |
| 2. | Concentrate | 4.0% |
| 3. | Busan 1030 (Mildewcide) | 2.0% |
| 4. | Tergitol 9N10 (Surfactant) | 0.7% |
| 5. | Fragrance | 0.8% |
| | | 100.0% |

Sources
A1. Robert A. Baldini & Co., Short Hills, N.J.
A2. AKZO NOBEL Chemicals, McCook, Ill.
A4. Dow Corning Corp., Midland, Mich.
C3. Buckman Laboratories, Memphis, Tenn.
C4. Union Carbide, Danbury, Conn.

Various formulations using different concentrations of Busan 1030, as well as formulations using varying concentrations of Troy Polyphase P20T were prepared. In addition, control formulations containing no mildewcidal compounds were also prepared. These were further tested as follows.

COMPOSITION TESTING

Comparative questions were posed:
1. Would the addition of mildewcide to the aqueous compositions of the present invention impart mildew resistance to the residual film?
2. Is the method of this invention more effective, less effective, or just as effective as the apply and dry method at resisting mildew?
3. Busan 1030 proved slightly more effective when used with the apply and dry method than did Troy Polyphase P20T, but would it also prove more effective when used in the method as proposed in this invention?

For the purpose of performing a blind study, two outside firms were supplied code-labeled samples of the preferred compositions which contained various loadings of Busan 1030 and Troy Polyphase P20T. Two samples contained no mildewcide. The samples were then tested for mildew resistance in special closed chambers designed for that purpose.

After four weeks in the chamber, the two samples containing no mildewcide evidenced no mildew resistance whatsoever. All others rated excellent.

In answer to the above questions:
1. The method and composition of the present invention did, in fact, impart excellent mildew resistance.
2. For comparable percentages of mildewcide loading, this method actually proved more effective than the apply and dry method.
3. Even though Troy Polyphase P20T rated excellent, Busan 1030 again rated slightly more effective than Troy Polyphase P20T.

EXAMPLE 2

In light of the results of Example 1, the following questions were posed:
1. Would the mildew-resistant film deposited by the method of the present invention be a durable film able to impart mildew resistance to surfaces outdoors for extended time periods, as compared with its effectiveness in the 4 week indoor testing conditions of Example 1?
2. What concentration of Busan 1030 would be optimally effective for use in outdoor conditions?
3. Would the addition of Busan 1030 to commercially available "wash-and-wax," apply-and-rinse products likewise impart effective mildew resistance to the films these products deposit?

To answer these questions, an independent laboratory in Florida was provided with code-labeled samples of 0%, 1%, 2%, 3%, and 4% Busan 1030 formulations: one series of said samples containing the same film-formers as and prepared as in Example 1, and another series of said samples containing instead Tannery® Wash 'N Wax® (a retail wash-and-wax, spray and rinse product manufactured by L & W Products, Bloomington, Ind.) which had been diluted in accordance with the manufacturer's instructions prior to addition of Busan 1030.

Each of these sample compositions was applied to a wooden panel and exposed to the outdoor conditions of Florida's humid climate for a 12-month period. At 12 months, all panels treated with samples containing Busan 1030—both those containing the film formers of Example 1 and those containing the Tannery® Wash 'N Wax®—showed mildew resistance. In contrast, all panels treated with the samples containing no Busan 1030 exhibited no mildew resistance. They were literally black with mildew.

As measured on a mildew-resistance scale of 1–10, with a rating of 10 indicating perfect resistance, the samples containing 1%, 2%, or 3% Busan 1030 imparted moderate mildew resistance to treated surfaces, the surfaces of these panels being graded 2–5. The samples containing 4% Busan 1030 imparted a high degree of mildew resistance to treated surfaces, the surfaces of these panels being graded at least 8, with no signs of mildew growth visible to the human eye.

Based on these results, the questions posed are answered as follows:

1. Yes, the film deposited by the method of the present invention is sufficiently durable to impart mildew resistance to surfaces in outdoor conditions and for extended time periods.
2. A 4% concentration of Busan 1030 (30% active ingredient, providing 1.2% active ingredient to the present composition) appears to be the most effective of all concentrations tested.
3. Yes, the use of commercially available "wash-and-wax," apply-and-rinse products appears to be equally effective for imparting mildew resistant films as the film-forming materials used in Example 1.

It should be noted that the Busan-containing samples used in the tests reported in the above Examples employed Busan 1030 which was the material then available. More recently, Busan 1200 has been made available. Busan 1200 contains the same concentration of the same active ingredient as Busan 1030 and is more environmentally friendly while being equally effective. Busan 1200 is therefore the more preferred mildewcide compound-containing mixture.

The above description is considered that of the preferred embodiments only. Modifications of the invention will occur to those skilled in the art and to those who make or use the invention. Therefore, it is understood that the embodiments described above are merely for illustrative purposes and not intended to limit the scope of the invention, which is defined by the following claims as interpreted according to the principles of patent law, including the doctrine of equivalents.

The invention claimed is:

1. A method for applying a mildewcide compound laden film to at least one surface by applying a mildewcide compound-containing, film-depositing, aqueous composition onto said surface, allowing to stand momentarily, and rinsing with water, said mildewcide compound laden film remaining upon said surface after said rinsing, wherein said composition comprises:
   a) at least one wax,
   b) at least one fatty amine,
   c) at least one amino silicone,
   d) at least one non-ionic surfactant,
   e) at least one mildewcide compound, and
   f) an aqueous solvent.

2. The method as set forth in claim 1, wherein said aqueous composition comprises:
   a) at least one wax in the range of about 0.1% to about 2% wt/wt,
   b) at least one fatty amine in the range of about 0.01% to about 2% wt/wt,
   c) at least one amino silicone in the range of about 0.01% to about 1% wt/wt,
   d) at least one non-ionic surfactant in the range of about 0.1% to about 5% wt/wt,
   e) at least about 0.05% wt/wt of a mildewcide compound or compounds, and
   f) the balance an aqueous solvent.

3. The method as set forth in claim 2 wherein said aqueous composition is allowed to stand for a period of about 30 to about 60 seconds.

4. The method as set forth in claim 2 wherein said aqueous composition contains at least one natural wax in the range of about 0.1% to about 2% wt/wt.

5. The method as set forth in claim 2 wherein said wax is carnauba wax.

6. The method as set forth in claim 5 wherein said carnauba wax is present at a concentration of about 0.2% to about 0.5% wt/wt.

7. The method as set forth in claim 6 wherein said carnauba wax is present at a concentration of about 0.264% wt/wt.

8. The method as set forth in claim 2 wherein said aqueous composition contains about 0.01% to about 2% wt/wt of at least one fatty amine conforming to the following structure:

wherein n is an integer ranging from 15–19.

9. The method as set forth in claim 2 wherein said aqueous composition contains about 0.05% to about 0.1% wt/wt of at least one fatty amine conforming to the following structure:

wherein n=17.

10. The method as set forth in claim 2 wherein said aqueous composition contains about 0.01 to about 1% wt/wt of at least one amino silicone conforming to the following structure:

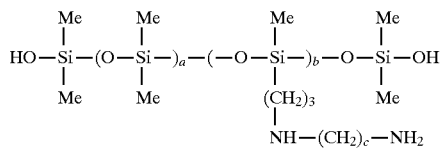

wherein a is 100–1000, b is 1–10, and c is 2–4.

11. The method as set forth in claim 2 wherein said aqueous composition contains about 0.1% to about 1% wt/wt of a least one amino silicone conforming to the following structure:

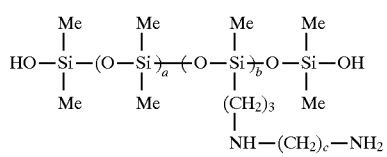

wherein a is 150–500, b is 2–5, and C is 2.

12. The method as set forth in claim 2 wherein said aqueous composition contains a mildewcide compound selected from:
   a. 2-(Thiocyanomethylthio)benzothiazole;
   b. 3-Iodo-2-propynyl butyl carbamate;
   c. 2,4,5,6-Tetrachloro-isophthalonitrile;
   d. 2-(4-Thiazolyl) benzimidazole;

e. 2-N-Octyl-4-isothiazolin-3-one;
f. Diiodomethyl p-tolyl sulfone; and
g. Mixtures thereof.

13. The method as set forth in claim 2 wherein said aqueous composition contains about 0.4% to about 2.5% wt/wt of either 2-(Thiocyanomethylthio)benzothiazole or 3-Iodo-2-propynyl butyl carbamate or a mixture thereof.

14. The method as set forth in claim 2 wherein said aqueous composition contains about 0.1% to about 5% wt/wt of at least one non-ionic surfactant conforming to the following structure:

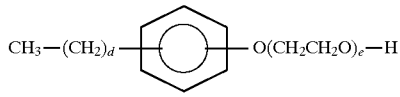

wherein d is an integer ranging from 5 to 12, and e is an integer ranging from 4 to 12.

15. The method as set forth in claim 2 wherein said aqueous composition contains about 0.5% to about 1% wt/wt of at least one non-ionic surfactant conforming to the following structure:

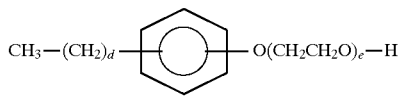

wherein d is an integer ranging from 5 to 12, and e is the integer 9.

16. The method as set forth in claim 2 wherein said aqueous composition contains water in the range of about 85% to about 99%.

17. An aqueous, film-depositing, mildewcidal composition comprising:
   a) at least one wax in the range of about 0.1% to about 2% wt/wt,
   b) at least one fatty amine in the range of about 0.01% to about 2% wt/wt,
   c) at least one amino silicone in the range of about 0.01% to about 1% wt/wt,
   d) at least one non-ionic surfactant in the range of about 0.1% to about 5% wt/wt,
   e) at least about 0.05% wt/wt of a mildewcide compound or compounds, and
   f) the balance an aqueous solvent.

18. The composition of claim 17 wherein said composition contains at least one natural wax in the range of about 0.1% to about 2% wt/wt.

19. The composition of claim 17 wherein said wax is carnauba wax.

20. The composition of claim 19 wherein said carnauba wax is present at a concentration of about 0.2% to about 0.5% wt/wt.

21. The composition of claim 20 wherein said carnauba wax is present at a concentration of about 0.264% wt/wt.

22. The composition of claim 17 wherein said composition contains about 0.01% to about 2% wt/wt of at least one fatty amine conforming to the following structure:

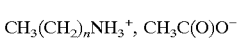

wherein n is an integer ranging from 15–19.

23. The composition of claim 22 wherein said composition contains about 0.05% to about 0.1% wt/wt of at least one fatty amine conforming to the following structure:

wherein n=17.

24. The composition of claim 17 wherein said composition contains about 0.01 to about 1% wt/wt of at least one amino silicone conforming to the following structure:

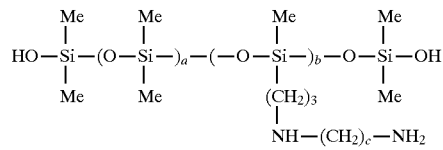

wherein a is 100–1000, b is 1–10, and c is 2–4.

25. The composition of claim 24 wherein said composition contains about 0.1% to about 1% wt/wt of at least one amino silicone conforming to the following structure:

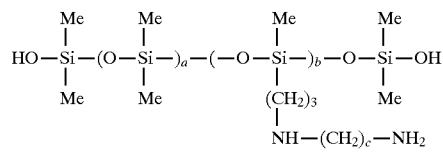

wherein a is 150–500, b is 2–5, and c is 2.

26. The composition of claim 17 wherein said composition contains a mildewcide selected from:
   a. 2-(Thiocyanomethylthio)benzothiazole;
   b. 3-Iodo-2-propynyl butyl carbamate;
   c. 2,4,5,6-Tetrachloro-isophthalonitrile;
   d. 2-(4-Thiazolyl) benzimidazole;
   e. 2-N-Octyl-4-isothiazolin-3-one;
   f. Diiodomethyl p-tolyl sulfone; and
   g. Mixtures thereof.

27. The composition of claim 17 wherein said composition contains about 4% to about 7% wt/wt of a mildewcide compound-containing mixture containing either 2-(Thiocyanomethylthio)benzothiazole or 3-Iodo-2-propynyl butyl carbamate or a mixture thereof.

28. The composition of claim 26 wherein said composition contains either 2-(Thiocyanomethylthio)benzothiazole or 3-Iodo-2-propynyl butyl carbamate or a mixture thereof in the range of about 0.4% to about 2.5% wt/wt.

29. The composition of claim 17 wherein said composition contains about 0.1% to about 5% wt/wt of at least one non-ionic surfactant conforming to the following structure:

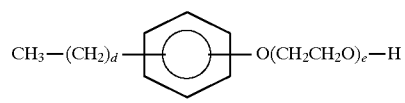

wherein d is an integer ranging from 5 to 12, and e is an integer ranging from 4to 12.

30. The composition of claim 29, wherein said composition contains about 0.5% to about 1% wt/wt of at least one non-ionic surfactant conforming to the following structure:

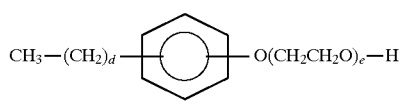
wherein d is an integer ranging from 5 to 12, and e is the integer 9.
31. The composition of claim 17 wherein said composition contains water in the range of about 85% to about 99%.
* * * * *